United States Patent
Petering et al.

(10) Patent No.: US 9,709,526 B2
(45) Date of Patent: Jul. 18, 2017

(54) NATIVE PROTEIN ELECTROPHORESIS AND METHODS OF USE

(71) Applicant: UWM Research Foundation, Inc., Milwaukee, WI (US)

(72) Inventors: David H. Petering, Fox Point, WI (US); William J. Wobig, Jackson, WI (US); Andrew Nowakowski, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 10 days.

(21) Appl. No.: 14/258,160

(22) Filed: Apr. 22, 2014

(65) Prior Publication Data

US 2014/0311908 A1     Oct. 23, 2014

Related U.S. Application Data

(60) Provisional application No. 61/814,609, filed on Apr. 22, 2013.

(51) Int. Cl.
*G01N 27/447* (2006.01)
*C07K 1/26* (2006.01)

(52) U.S. Cl.
CPC ............ *G01N 27/447* (2013.01); *C07K 1/26* (2013.01); *G01N 27/44747* (2013.01)

(58) Field of Classification Search
CPC .. G01N 27/447; G01N 27/44747; C07K 1/26; B01D 57/02
See application file for complete search history.

(56) References Cited

PUBLICATIONS

Tyagi et al., Electrophoresis, 1993, 14, 826-828.*
Nature Protocols, 2006, 1, 418.*
Anderegg, G et al. "Pyridine Derivatives as Complexing Agents XI. Thermodynamics of Metal Complex Formation with Bis-, Tris- and Tetrakis [(2-pyridyl) methyl]-amines," 60. pp. 123-140 (1977).
Andrews, J.C. et al., "Characterization of N-(6-MEthoxy-8-Quinolyl)-p-Toluenesulfonamide for the detection of zinc in living sperm cells," Cytometry, vol. 21, pp. 153-159 (1995).
Back, C. J. et al., "Ca2+ and Zn2+ Dependence of DNA Synthesis in Untransformed and in Ha-rasval-12-Expressing NIH 3T3 Cells," Experimental Cell Research, vol. 208, pp. 303-310 (1993).
Ballestin, R., et al., "Ethanol Reduces Zincosome Formation in Cultured Astrocytes," Alcohol and Alcoholism, vol. 46, pp. 17-25 (2011).

(Continued)

*Primary Examiner* — Gurpreet Kaur
(74) *Attorney, Agent, or Firm* — Michael Best & Friedrich LLP (57) ABSTRACT

A method of characterizing proteins has been developed that includes providing a sample that contains a plurality of proteins to be characterized, wherein at least a first protein of the plurality of proteins is in its native form. Additionally, the method includes contacting the sample containing the plurality of proteins with a solution to form a sample solution, and then contacting the sample solution with a gel. The plurality of proteins is subsequently separated via electrophoresis within the gel, which includes an electrophoresis solution.

12 Claims, 4 Drawing Sheets

(56) References Cited

PUBLICATIONS

Barnett, J., et al., "Protein Fractionation and Detection for Metalloproteomics: Challenges and Approaches," Anal Bioanal Chem, vo. 402, pp. 3311-3322 (2012).

Bayer, E.A., et al., "Sodium Dodecyl Sulfate-Polyacrylamide Gel Electrophoretic Method for Assessing the Quaternary State and Comparative Thermostability of Avidin and Stretavidin," Electrophoresis, vol. 17, pp. 1319-1324 (1996).

Becker, J.S. et al, "Metal imaging in non-denaturing 2D electrophoresis gels by laser ablation inductively coupled plasma mass spectrometry (LA-ICP-MS) for the detection of metalloproteins" Metallomics, vol. 1, pp. 312-316 (2009).

Becker, J.S. et al., "Determination of Phosphorus-, Copper-, and Zinc-Containing Human Brain Proteins by LA-ICPMS and MALDI-FTICR-MS," Anal. Chem., vol. 77, pp. 5851-5860 (2005).

Becker, J.S. et al., "Imaging of Metals, Metalloids, and Non-metals by Laser Ablation Inductively Coupled Plasma Mass Spectrometry (LA-ICP-MS) in Biological Tissues," Mass Spectrometry Imaging, eds. S. S. Rubakhin and J. V. Sweedler, Humana Press, vol. 656, pp. 51-82 (2010).

Becker, J.S., et al., "In-gel Screening of Phosphorus and Copper, Zinc and Iron in Proteins of Yeast Mitochondria by LA-ICP-MS and Identification of Phosphorylated Protein Structures by MALDI-FT-ICR-MS after Separation with Two-Dimensional Gel Electrophoresis," J. Anal. At. Spectrom., vol. 19, pp. 1236-1243 (2004).

Bernhardt, M. et al., "Zinc Requirement During Meiosis I-Meiosis II Transitiion in Mouse Oocytes is Independent of the MOS-MAPK Pathway," Biol. Reprod., vol. 84, pp. 526-536 (2011).

Blonde, D.J., "The Effects of Ions and Freeze-Thawing on Supernatant and Mitochonrial Malate Dehydrogenase," Canadian Journal of Biochemistry, vol. 45, pp. 641-650 (1967).

Bortolato, M. et al., "Role of metal ions on the secondary and quaternary structure of alkaline phosphatase from bovine intestinal mucosa," Proteins: Structure, Function, and Bioinformatics, vol. 37, pp. 310-318 (1999).

Brewer, G.J. et al., "An introduction to isozyme techniques," Academic Press (1970).

Camacho-Carvajal, M.M. et al., "Two-dimensional Blue Native/SDS Gel Electrophoresis of Multi-Protein Complexes from Whole Cellular Lysates," Molecular & Cellular Proteomics, vol. 3, pp. 176-182 (2004).

Chatterjee, A. et al., "Thermodynamics of Micelle Formation of Ionic Surfactants: A Critical Assessment for Sodium Dodecyl Sulfate, Cetyl Pyridinium Chloride and Dioctyl Sulfosuccinate (Na Salt) by Microcalorimetric, Conductometric, and Tensiometric Measurements," The Journal of Physical Chemistry B, vol. 105, pp. 12823-12831 (2001).

Cuajungco, M.P. et al., "Nitric oxide generators produce accumulation of chelatable zinc in hippocampal neuronal perikarya," Brain Research vol. 799, pp. 118-129 (1998).

Cvetkovic, A. et al., "Microbial metalloproteomes are largely uncharacterized," Nature, vol. 466, pp. 779-782 (2010).

Esteban-Fernandez, D. et al., "Analytical methodologies for metallomics studies of antitumor Pt-containing drugs," Metallomics, vol. 2, pp. 19-38 (2010).

Fahrni, C.J. et al., "Aqueous Coordination Chemistry of Quinoline-Based Fluorescence Probes for the Biological Chemistry of Zinc," J. Am. Chem. Soc., vol. 121, pp. 11448-11458 (1999).

Finney, L. et al., "Eimaging Metals in Proteins by Combining Electrophoresis with Rapid X-ray Fluorescence Mapping," ACS Chemical Biology, vol. 5, pp. 577-587 (2010).

Flinn, J.M. et al., "Enhanced zinc consumption causes memory deficits and increased brain levels of zinc," Physiology & Behavior, vol. 83, pp. 793-803 (2005).

Fujiwara, Y. et al., "Repair of wounded monolayers of cultured vascular endothelial cells after simultaneous exposure to lead and zinc," Toxicology Letters vol. 94, pp. 181-188 (1998).

Fukamachi, Y. et al., "Zinc Suppresses Apoptosis of U937 Cells Induced by Hydrogen Peroxide through an Increase of the Bcl-2/Bax Ratio," Biochem. Biophys. Res. Commun., vol. 246, pp. 364-369 (1998).

Gibon, J. et al., "The thiol-modifying agent N-ethylmaleimide elevates the cytosolic concentration of free Zn2+ but not of Ca2+ in murine cortical neurons," Cell Calcium, vol. 48, pp. 37-43 (2010).

Gregory, J. D., "The Stability of N-Ethylmaleimide and its Reaction with Sulfhydryl Groups," J. Am. Chem. Soc., vol. 77, pp. 3922-3923 (1955).

Haase, H. et al., "Zinc ions cause the thimerosal-induced signal of fluorescent calcium probes in lymphocytes," Cell Calcium, vol. 45, pp. 185-191 (2009).

Hartung, H. et al., "Chemical regulators have overreached," Nature, vol. 460, pp. 208-212 (2009).

Hendrickson, K.M. et al., "Complexation of zinc(II) and other divalent metal ions by the fluorophore 2-methyl-8-(toluene-p-sulfonamido)-6-quinolyloxyacetic acid in 50% aqueous ethanol," J. Chem. Soc., Dalton Trans., pp. 3879-3882 (1997).

Hendrickson, K.M. et al.,"Coordination and Fluorescence of the Intracellular Zn2+ Probe [2-methyl-8-(4-Toluenesulfonamido)-6-quinolyloxy]acetic Acid (Zinquin A) in Ternary Zn2+ Complexes," J. Am. Chem. Soc., vol. 125, pp. 3889-3895 (2003).

Ho, L.H. et al., "Involvement of Intracellular Labile Zinc in Suppression of DEVD-Caspase Activity in Human Neuroblastoma Cells," Biochem. Biophys. Res. Commun., vol. 268, pp. 148-154 (2000).

Hulce, J.J. et al., "Proteome- wide mapping of cholesterol-interaction proteins in mammalian cells," Nature Methods, vol. 10, pp. 259-263 (2013).

Human Genome Sequencing Consortium, "Finishing the euchromatic sequence of the human genome," Nature, vol. 431, pp. 931-945 (2004).

Jimenez, M.S. et al., "Metal-protein binding losses in proteomic studies," Talanta, vol. 81, pp. 241-247 (2010).

Jornvall, H. et al., "Extended Superfamily of Short Alcohol-polyol-sugar Dehydrogenases: Structural Similarities bewteen Glucose and Ribitol Dehydrogenases," Eur. J. Biochem, vol. 72, pp. 425-442 (1977).

Kahakachchi, L. et al., "Identification and Characterization of Gadolinium(III) Complexes in Biological Tissue Extracts," Metallomics vol. 2, pp. 490-497 (2010).

Kamal, A.H. et al., "The wheat chloroplastic proteome," Journal of Proteomics, vol. 93, pp. 326-342 (2013).

Keele, B.B. et al., "Further Characterization of Bovine Superoxide Dismutase and Its Isolation from Bovine Heart," J. Biol. Chem., vol. 246, pp. 2875-2880 (1971).

Kemsley, J., "Merging Metals into Proteomics," Chemical & Engineering News Archive, vol. 89, pp. 28-30 (2011).

Kimura, E. et al., "Recent development of zinc-fluorophores," Chem. Soc. Rev., vol. 27, pp. 179-184 (1998).

Krezel, A. et al., "Zinc-buffering capacity of a eukaryotic cell at physiological pZn," J. Biol. Inorg. Chem., vol. 11, pp. 1049-1062 (2006).

Laemmli, U.K., "Cleavage of Structural Proteins during the Assembly for the Head of Bacteriophage T4," Nature, vol. 227, pp. 680-685 (1970).

Lakowicz, J. R., "Principles of Fluorescence Spectroscopy," Springer, ed. 3, (2006).

Lasserre, J. et al., "A complexomic study of *Escherichia coli* using Two-dimensional Blue Native/SDS Polyacrylamide Gel Electrophoresis," Electrophoresis, vol. 27, pp. 3306-3321 (2006).

Lindskog, S. et al., "Metal binding and catalytic activity in bovine carbonic anhydrase*," J. Biol. Chem., vol. 237, pp. 1129-1137 (1962).

Lu, H. et al., "Effects of intracellular zinc depletion on the expression of VDAC in cultured hippocampal neurons," Nutr. Neurosci., vol. 14, pp. 80-87 (2011).

Maggini, S. et al., "Essential Role of Vitamin C and Zinc in Child Immunity and Health," Journal of International Medical Research) vol. 38, pp. 386-414 (2010).

(56) References Cited

OTHER PUBLICATIONS

Malmgren, L. et al., "Uptake and Retrograde Axonal Transport of Various Exogenous Macromolecules in Normal and Crushed Hypoglossal Nerves," Brain Research, vol. 153, pp. 477-493 (1978).

Manchenko, G., "Handbook of detection of enzymes on electrophoretic gels," CRC Press, ed. 2, (2003).

Marklund, S. L. et al."Superoxide dismutase in extracellular fluids," Clinica Chimica Acta, vol. 126, pp. 41-51 (1982).

Marklund, S.L., "Human copper-containing superoxide dismutase of high molecular weight," Proceedings of the National Academy of Sciences, vol. 79, pp. 7634-7638 (1982).

Masuoka, J. et al., "Zinc(II) and copper(II) binding to serum albumin. A comparative study of dog, bovine, and human albumin," The Journal of Biological Chemistry, vol. 269, pp. 25557-25561 (1994).

Mathewson, P. R. et al., "The absence of zinc in the mitochondrial and supernatant forms of malate dehydrogenase," Biochimica et Biophysica Acta, vol. 321, pp. 413-422 (1973).

McDougall, G., "A comparison of proteins from the developing xylem of compression and non-compression wood of branches of Sitka spruce (*Picea sitchensis*) reveals a differentially expressed laccase," J Exp. Botany, vol. 51, pp. 1395-1401 (2000.).

Meeusen, J.W. et al., "TSQ (6-Methoxy-8p-Toluenesulfonamido-Quinoline), a Common Fluorescent Sensor for Cellular Zinc, Images Zinc Proteins," Inorganic Chemistry, vol. 50, pp. 7563-7573 (2011).

Meister, A., "Glutathione metabolism and its selective modification," J. Biol. Chem., vol. 263, pp. 17205-17208 (1988).

Mena, L. et al., "OFFGEL Isoelectric Focusing and Polyacrylamide Gel Electrophoresis Separation of Platinum-binding Proteins," Journal of Chromatography A, vol. 1218, pp. 1281-1290 (2011).

Muylle, F. R. et al. "Tracing of labile zinc in live fish hepatocytes using FluoZin-3," BioMetals vol. 19, pp. 437-450 (2006).

Namdarghanbari, M. A. et al., "Reaction of the zinc sensor FluoZin-3 with Zn7-metallothionein: Inquiry into the existence of a proposed weak binding site," J. Inorg. Biochem., vol. 104, pp. 224-231 (2010).

Nowakowski et al., "Fluorescent Zn2+ sensor chemical biology—reexamination of possible intracellular targets," 3rd Canadian Conference of Biological Inorganic Chemistry, (2011).

Nowakowski et al., "Reactions of the Fluorescent Sensor, Zinquin, With the Zinc-Proteome: adduct Formation and Ligand Substitution," Inorg Chem., vol. 50, pp. 10124-10133 (2011).

Nowakowski et al., "Sensor specific imaging of proteomic Zn2+ with zinquin and TSQ after cellular exposure to N-ethylmaleimide," Metallomics, vol. 4, pp. 448-456 (2012).

Nowakowski et al., "The chemical biology of zinquin: what is being imaged?," 2nd Canadian Conference of Biological Inorganic Chemistry, (2009).

Polatajko, A. et al., "Combined Application of a Laser Ablation-ICP-MS assay for screening and ESI-FTICR-MS for Identification of a Cd-binding Protein in *Spinacia oleracea* L. after Exposure to Cd," Metallomics, vol. 3, pp. 1001-1008 (2011).

Pulido, P. et al., "Isolation and Some Properties of Human Metallothionein," Biochemistry, vol. 5, pp. 1768-1777 (1966).

Remmerie, N. et al., "Unraveling tobacco BY-2 protein complexes with BN PAGE/LC-MS/MS and clustering methods," Journal of Proteomics, vol. 74, pp. 1201-1217 (2011).

Richardson, A. et al., "A Laccase-type Polyphenol Oxidase from Lignifying Xylem of Tobacco," Phytochemistry, vol. 44, pp. 229-235 (1996).

Rosengarth, A. et al., "X-ray structure of full-length annexin 1 and implications for membrane aggregation," J. Mol. Biol., vol. 306, pp. 489-498 (2001).

Rudolf, E. et al., "Zinc has ambiguous effects on chromium (VI)-induced oxidative stress and apoptosis," J. Trace Elem. Med Biol., vol. 18, pp. 251-260 (2005).

Rush, T. et al.,"Glutathione-mediated neuroprotection against methylmercury neurotoxicity in cortical culture is dependent on MRP1," Neurotoxicology, vol. 33, pp. 476-81 (2011).

Sauer, G. R. et al., "Intracellular zinc fluxes associated with apoptosis in growth plate chondrocytes," J. Cell. Biochem., vol. 88, pp. 954-969 (2003).

Schagger, H. et al. "Blue Native Electrophoresis for Isolation of Membrane-Protein Complexes in Enzymatically Active Form," Analytical Biochemistry, vol. 199, pp. 223-231 (1991).

Schägger, H. et al. "Significance of Respirasomes for the Assembly/Stability of Human Respiratory Chain Complex I," J. Biol. Chem., vol. 279, pp. 36349-36353 (2004).

Schamel, W. W. A. et al., "Monomeric and oligomeric complexes of the B cell antigen receptor," Immunity, vol. 13, pp. 5-14 (2000).

Sensi, S. L. et al., "Zinc in the physiology and pathology of the CNS," Nature Reviews Neuroscience, vol. 10, pp. 780-791 (2009).

Sessler, N. et al., "Analysis of the Plasmodium falciparum proteasome using Blue Native PAGE and label-free quantitative mass spectrometry," Amino Acids, vol. 43, pp. 1119-1129 (2012).

Shaw III, C. F. et al., "Kinetics of reversible N-ethylmaleimide alkylation of metallothionein and the subsequent metal release," JBIC, vol. 2, pp. 65-73 (1997).

Shin, J.-H., J"Graded expression of zinc-responsive genes through two regulatory zinc-binding sites in Zur," Proceedings of the National Academy of Sciences, vol. 108, pp. 5045-5050 (2011).

Siegers, G. M. et al., "Different composition of the human and the mouse γδT cell receptor explains different phenotypes of CD3γ and CD3δ immunodeficiencies," The Journal of Experimental Medicine, vol. 204, pp .2537-2544 (2006).

Sillen, L.G. et al., "Stability constants of metal-ion complexes," Chemical Society, Burlington House, London (1971).

Snitsarev, V., "Fluorescent Detection of Zn2+-Rich Vesicles with Zinquin: Mechanism of Action in Lipid Environments," Biophys. J., vol. 80, pp. 1538-1546 (2001).

Stern, L. et al., "The Human Class II MHC protein HLA-DR1 assembles as empty αβ heterodimers in the absence of antigenic peptide," Cell, vol. 68, pp. 465-477 (1992).

Sussulini et al. "Combination of PAGE and LA-ICP-MS as an Analytical Workflow in Meallomics: State of the Art, New Quantification Strategies, Advantages and Limitations" Metallomics (2011) 3:1271-1279.

Tainer, J.A. et al., "Structure and Mechanism of Copper, Zinc Superoxide Dismutase," Nature, vol. 306, pp. 284-287 (1983).

Takagi, T. et al., "Binding Isotherms of Sodium Dodecyl Sulfate to Protein Polypeptides with Special Reference to SDS-polyacylamide Gel Electrophoresis," J. Biochem., vol. 77, pp. 939-947 (1975).

Takei, M. et al., "Femtosecond Time-Resolved Spectroscopy of Photoisomerization of Methyl Orange in Cyclodextrins," The Journal of Physical Chemistry A, vol. 105, pp. 11395-11399 (2001).

Taketa, K. "A tetrazolium method for peroxidase staining: Application to the antibody-affinity blotting of α-fetoprotein separated by lectin affinity electrophoresis," Electrophoresis, vol. 8, pp. 409-414 (1987).

Talian, I. et al, "Impact of un-polymerized acrylamide monomer residues onto protein identification by MALDI TOF MS," cent.eur.j.chem., vol. 10, pp. 1073-1078 (2012).

Tanaka, Y. et al., "Purification and Properties of β-Galactosidase from Aspergillus oryzae," J. Biochem., vol. 77, pp. 241-247 (1975).

Tatsumi, T. et al., "Hypochlorous Acid Mobilizes Intracellular Zinc in Isolated Rat Heart Myocytes," Journal of Molecular and Cellular Cardiology, vol. 26, pp. 471-479 (1994).

Thangthaeng, N. et al., "Nongradient blue native gel analysis of serum proteins and in-gel detection of serum esterase activities," Journal of Chromatography, vol. 879, pp. 386-394 (2011).

Trotman, C. N. et al., "Effects of zinc and other metal ions on the stability and activity of *Escherichia coli* alkaline phosphatase" Biochem J, vol. 124, pp. 25-30 (1971).

Truong-Tran, A. Q. et al., "New insights into the role of zinc in the respiratory epithelium," Immunology and Cell Biology, vol. 79, pp. 170-177 (2001).

(56) References Cited

OTHER PUBLICATIONS

Tsuchiya, D. et al., "Mild Hypothermia Reduces Zinc Translocation, Neuronal Cell Death, and Mortality After Transient Global Ischemia in Mice," J Cereb Blood Flow Metab, vol. 22, pp. 1231-1238 (2002).

Waldron, K. J., "How do bacterial cells ensure that metalloproteins get the correct metal?" Nature Reviews Micro, vol. 7, pp. 25-35 (2009).

Weber, K et al. "The Reliability of Molecular Weight Determinations by Dodecyl Sulfate-Polyacrylamide Gel Electrophoresis," 244. pp. 4406-4412 (1969).

Westermeier, R. et al., "Blue Native Gel Electrophoresis—a valuable tool in studying membrane protein complexes," American Electrophoresis Society, (2000-2014).

Wittig, I. et al. "Blue Native PAGE" Nature Protocols, vol. 1, pp. 418-428 (2006).

Wittig, I. et al., "Advantages and limitations of clear-native PAGE," Proteomics, vol. 5, pp. 4338-4346 (2005).

Wobig, W. J., "Methods in Metallomics, Proteomics, and Toxicology: Development and Applications of Laser Ablation Inductively Coupled Plasma Mass Spectrometry and Native SDS-PAGE," UW—Milwaukee, Milwaukee, (2013).

Yap, L. et al., "Determination of GSH, GSSG, and GSNO Using HPLC with Electrochemical Detection," Methods Enzymol., vol. 473, pp. 137-147 (2010).

Zhang, Y. et al., "Probing the viral mettalome: searching for metalloproteins in bacteriophage λ—the hunt begins," Metallomics, vol. 3, pp. 472-481 (2011).

Zhu, J. et al., "Reactivity of Zn-, Cd-, and Apo-Metallothionein with Nitric Oxide Compounds: In Vitro and Cellular Comparison," Chem. Res. Toxicol., vol. 23, pp. 422-431 (2010).

\* cited by examiner

NATIVE PROTEIN ELECTROPHORESIS AND METHODS OF USE

CROSS-REFERENCE TO RELATED APPLICATIONS

This application claims priority to U.S. Provisional Patent Application No. 61/814,609 filed Apr. 22, 2013, the content of which is incorporated herein by reference in its entirety.

STATEMENT REGARDING FEDERALLY SPONSORED RESEARCH

This invention was made with government support under the National Institute of Health (RO1 GM085114-01). The United States government has certain rights in the invention.

INTRODUCTION

A commonly used technology to obtain high resolution analytical separation of mixtures of proteins is sodium dodecyl sulfate polyacrylamide gel electrophoresis (SDS-PAGE). The procedure involves denaturation of proteins with an anionic detergent that binds to them, imparting to all proteins a negative charge proportional to their molecular mass. Due to this denaturation, an assessment of protein function following separation cannot be done.

An alternative is the blue-native PAGE technique (BN-PAGE). While this technique maintains native functionality of the separated protein, there is poor resolution of the separation. Accordingly, there is a need for protein separation techniques that offer high resolution while maintaining native functionality.

SUMMARY

In one embodiment, provided herein are methods of characterizing proteins. The methods may include providing a sample comprising a plurality of proteins to be characterized, wherein at least a first protein of the plurality of proteins is in its native form. The methods may further include contacting the sample with a solution to form a sample solution. Additionally, the methods may include contacting the aforementioned sample solution with a gel, and then separating the plurality of proteins within the sample solution by electrophoresis within the gel, wherein the gel comprises an electrophoresis solution. The sample solution may be substantially free of detergent. The sample solution may be at a temperature of less than 30° C. In some embodiments, the sample solution may be at a temperature of less than 10° C. The electrophoresis solution may include a detergent at a concentration of 0.02 wt % to 0.04 wt %. In some embodiments, the electrophoresis solution may include a detergent at a concentration of 0.0375 wt %. The detergent may include an alkyl-sulfate compound. The alkyl-sulfate compound may include sodium dodecyl sulfate. In some embodiments, separating the plurality of proteins may be performed at 4° C. In other embodiments, separating the plurality of proteins within the sample solution by electrophoresis within the gel comprises separating the plurality of proteins within the sample solution by electrophoresis within the gel such that two proteins which differ in molecular weight by 2 kDa can be distinguished from one another on a 12% polyacrylamide gel.

In some embodiments, the methods may include the first protein maintaining a native functionality. The native functionality may include enzymatic activity. In other embodiments, enzymatic activity can be provided at least in part by an enzyme that is chosen from the group consisting of dehydrogenase, galactosidase, dismutase, phosphatase, urease, oxidase, anhydrase, kinase, protease, and synthase. In various embodiments, the first protein can maintain its native interactions with at least one metal ion, wherein the at least one metal ion is an ion of a metal chosen from the group consisting of copper, magnesium, manganese, molybdenum, nickel, and zinc. In other embodiments, separating the plurality of proteins within the sample solution by electrophoresis within the gel includes separating the plurality of proteins within the sample solution by electrophoresis within the gel while the first protein is in its native form.

In another embodiment, provided herein are additional methods of characterizing proteins. The methods may include providing a sample with a plurality of proteins to be characterized, wherein at least a first protein of the plurality of proteins is in its native form; contacting the sample with a solution to form a sample solution, wherein the sample solution is substantially free of detergent; contacting the sample solution with a gel; and separating the plurality of proteins within the sample solution by electrophoresis within the gel, wherein the gel includes an electrophoresis solution comprising from 0.02 to 0.04 wt % detergent. In some embodiments, the electrophoresis solution may include a detergent at a concentration of 0.0375 wt %. The detergent may include sodium dodecyl sulfate. In various embodiments, the sample solution may be at a temperature of less than 10° C. Furthermore, separating the plurality of proteins may be performed at 4° C.

Other aspects of the invention will become apparent by consideration of the detailed description and accompanying drawings.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

DEFINITIONS

"Native form," as used herein, refers to providing a characterized protein that possesses the ability to perform one or more biological functions that said protein would be able to perform within its native environment.

"Substantially free of" a particular compound, as used herein, refers to a composition to which the compound has not been deliberately added such that the composition is largely or approximately free of the compound, outside of trace quantities or impurities of the compound.

METHODS OF CHARACTERIZING PROTEINS VIA NATIVE SDS PAGE (NSDS-PAGE)

Disclosed herein are methods of characterizing a plurality of proteins at high resolution, while maintaining said proteins' native functionality. In some embodiments, the methods include providing a sample comprising a plurality of proteins to be characterized, wherein at least a first protein of the plurality of proteins is in its native form. In other embodiments, the methods further include contacting the sample from the prior step with a solution to form a sample solution. The sample solution may then be contacted with a gel. The plurality of proteins, within the sample solution, may then be separated by electrophoresis within the aforementioned gel, wherein the gel includes an electrophoresis solution. In still other embodiments, the methods further include separating the plurality of proteins at reduced temperatures, for example at 4° C. Additionally, in various embodiments the methods include separating the plurality of proteins electrophoretically at 150 V to 200 V. For example, separating the plurality of proteins electrophoretically may be done at 150 V, 160 V, 170 V, 180 V, 190 V, or 200V.

In other embodiments, the methods further include separating the plurality of proteins within the sample solution by electrophoresis within the gel, wherein the first protein is maintained in its native form. The native form of the first protein may be detected using a number of techniques, for example based on antibody detection. Additionally, the first protein may be separated and maintained in its native functional form. In still other embodiments, the methods also include separating proteins in conditions that maintain their native functionality, wherein native functionality can include enzymatic activity. Enzymatic activities may include, but are not limited to, dehydrogenase, galactosidase, dismutase, phosphatase, urease, oxidase, anhydrase, kinase, protease, and synthase activities.

Furthermore, native functionality of the separated proteins may include the ability to interact with at least one metal ion, which may include metal cofactors. Additionally, the metal ion may be, but is not limited to, an ion of copper, manganese, molybdenum, nickel, zinc, cadmium, mercury, lead, arsenic, chromium, titanium, iron, cobalt, gallium, gold, platinum, vanadium, tungsten, uranium, gadolinium, tin and bismuth. The methods may be used for investigating relationships with metals and proteins. For example, technology to obtain detailed information about cellular distribution and trafficking of biologically essential, toxic, and therapeutic metals has been emerging. The evolution of elemental detection methodology has begun to make possible the identification of metal ions associated with biomolecules that are isolated from cell extracts and ultimately separated electrophoretically within the solid matrix of polyacrylamide gel.

Once the protein of interest has been separated and maintained in its native, functional form, it may be further characterized with one of a number of analysis techniques. Among the techniques that may be used is laser ablation-inductively coupled plasma-mass spectrometry (LA-ICP-MS). Once metals are located in association with protein bands, protein identity can be determined by mass spectrometry. Nevertheless, these methods have not been widely or effectively utilized. The challenge in applying LA-ICP-MS or other analytical methods to detect elements in metallo-proteomic studies has been the lack of reliable methods to separate the proteome with high resolution while retaining bound metal ions, particularly in the final electrophoresis preceding metal analysis.

Accordingly, the disclosed invention provides methods for performing electrophoresis of proteins under conditions which preserve the native conformation and enzymatic functionality of at least some of the proteins, so that the proteins can be assayed following separation. For example, the proteins can be assayed in situ within the separation gel, or following elution from the gel. In contrast to conventional electrophoresis methods (e.g. SDS-PAGE), the disclosed methods are designed to minimize or avoid denaturation of the proteins before, during, and after the separation process. Agents that are typically added to electrophoresis sample buffers and/or running buffers such as detergents, disulfide reducing agents (e.g. dithiolthreitol or β-mercaptoethanol), metal chelating agents (e.g. EDTA, EGTA, DTPA, etc.), and even heat, are reduced or eliminated, so as to maintain the proteins' native state. Nevertheless, the disclosed techniques have been used to separate proteins with surprisingly improved levels of resolution compared to other attempts at native protein separation.

A. Sample Solution

The methods of characterizing a plurality of proteins may comprise a sample solution. The sample solution may be substantially free of detergents, metal chelation agents, and/or reducing agents. Metal chelation agents may interfere with protein/metal ion interactions. In contrast to typical sample preparation for electrophoresis (e.g. SDS-PAGE) which is performed at elevated temperatures to encourage denaturation of the proteins, the sample solution according to embodiments of the presently-disclosed invention may not be heated and instead may be maintained at a temperature less than 30° C. For example, the sample solution may be maintained at a temperature less than 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., or 0° C.

B. Electrophoresis Solution

The disclosed methods of characterizing a plurality of proteins may comprise an electrophoresis solution in which samples are electrophoretically separated within a gel. The electrophoresis solution may be substantially free of metal chelation agents, as discussed above, although the electrophoresis solution may include detergent, but generally at a low concentration. The detergent may be at a concentration between 0.02 wt % and 0.04 wt %. For example, the detergent may be at a concentration of 0.02 wt %, 0.022 wt %, 0.025 wt %, 0.024 wt %, 0.025 wt %, 0.026 wt %, 0.0275 wt %, 0.028 wt %, 0.03 wt %, 0.032 wt %, 0.0325 wt %, 0.034 wt %, 0.035 wt %, 0.036 wt %, 0.0375 wt %, 0.038 wt %, or 0.04 wt %. The detergent generally has a net charge and may be anionic or cationic. In some embodiments, the detergent may include an alkyl-sulfate compound, which may include, but is not limited to, sodium octyl sulfate, sodium decyl sulfate, sodium dodecyl sulfate (SDS), and combinations thereof. In various embodiments, the alkylsulfate compound may include alkyl chains of differing lengths from 1 to 20. Since detergents bind stoichiometrically with proteins, the detergent (e.g. SDS) added to the electrophoresis solution helps to probe the presence, relative concentration, purity of proteins, the proteins' approximate molecular mass, and, in conjunction with immunochemical methods or mass spectrometry, the identity and possible covalent modifications of the proteins. However, because conventional SDS-PAGE techniques require protein denaturation prior to electrophoresis, these techniques cannot be used for identification of non-covalent components of native proteins or protein complexes such as metal ions, or to study features of protein function. Importantly, proteomic-level studies directed at uncovering properties of native protein structures, including non-covalent cofactors, cannot be conducted with SDS-PAGE. Thus, the disclosed invention addresses this problem by providing methods and systems for conducting electrophoresis under conditions in which proteins may maintain their native conformations and functionalities.

A further precaution that can be taken to avoid denaturation of the sample proteins is to perform electrophoresis at reduced temperatures, for example room temperature (e.g. 22° C.) or less. Thus, in various embodiments the electrophoresis buffer may be maintained at, and electrophoresis performed at, a temperature less than 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., or 0° C.

EXAMPLES

The foregoing may be better understood by reference to the following examples, which are presented for purposes of illustration and are not intended to limit the scope of the invention.

Example 1. Characterization of Native SDS-PAGE

Pre-casts PAGE gels and corresponding buffers were purchased from Invitrogen. Chemicals were obtained in the highest available purity from Sigma-Aldrich or Fisher Scientific. Several Zn-proteins were utilized in the study, including yeast alcohol dehydrogenase (Zn-ADH), bovine alkaline phosphatase (Zn-AP), superoxide dismutase (Cu, Zn-SOD), and carbonic anhydrase (Zn-CA). Each was purchased from Sigma-Aldrich and used without further purification. Lyophilized enzymes (10 mg/mL) were dissolved in degassed 20 mM Tris-Cl pH 7.4, stored at 4° C., and used within one month of rehydration. Other enzymes and proteins were also obtained from Worthington Biochemical.

Pig Kidney Epithelial Cells (LLC-PK$_1$) were grown under level 1 culture conditions in M199 media (Sigma) supplemented with 4% FCS, 50 mg/L Streptomycin, and 50 mg/L Penicillin G in an atmosphere containing 5% $CO_2$ at 37° C. Once cells had reached confluence, media was decanted and culture plates were washed 3× in cold Dulbecco's phosphate buffered saline (DPBS).

Cells were scraped using a rubber cell scraper into DPBS and collected via centrifugation at 680×g before resuspension in 1 mL cold dd$H_2O$ per 10 plates. The cell suspension was sonicated and 500 µM phenylmethylsulfonyl fluoride (PMSF) and 1000 U Benzonase© nuclease (Sigma) were added to inhibit proteolysis and increase nuclease activity, respectively. The sonicate was centrifuged at 47,000×g for 30 minutes at 4° C. to remove cellular debris and the supernatant loaded onto a Sephadex G-25 (GE Healthcare) gel filtration column and eluted with degassed 5 mM Tris-Cl pH 8.0. Fractions in the high molecular weight region exhibiting absorbance at 280 nm were pooled as the proteome (lacking low molecular weight species) and subsequently loaded onto a Macro-Prep DEAE anion exchange column (Bio-Rad) for further separation. The column was eluted with 5 mM Tris-Cl pH 8.0 with a 50 mM NaCl stepwise gradient from 0-500 mM NaCl. Select fractions were concentrated using a Millipore centrifuge filter (3,000 Da molecular weight cut-off) that was spun at 12,000×g for 20 minutes at 4° C. Samples were desalted by repeating the concentration three times, washing the protein sample with fresh 5 mM Tris-Cl pH 8.0 for each concentration.

Denaturing SDS-PAGE was performed according to the Invitrogen NuPAGE® specifications. In brief, 7.5 µL of protein sample (5-25 µg protein) were mixed with 2.5 µL of 4×LDS sample loading buffer (Invitrogen) and heated at 70° C. for 10 min. Samples were then loaded into precast NuPAGE Novex 12% Bis-Tris 1.0 mm minigels (Invitrogen). Then, 5 µL of Pre-stained SDS-PAGE Standards (Bio-Rad) were loaded in each gel run. Electrophoresis was performed at room temperature for approximately 45 min using a constant voltage (200V) in 1× solution of NuPAGE MOPS SDS running buffer (Invitrogen) until the dye front reached the end of the 60 mm gel. Buffer compositions were obtained from the manufacture's technical guide and are listed in Table 1.

Blue Native (BN)-PAGE was also performed according to the manufacture's protocol. In this procedure, 7.5 µL of protein sample were mixed with 2.5 µL of 4× BN-PAGE sample buffer (Invitrogen) and loaded into precast NativePAGE Novex 4-16% Bis-Tris 1.0 mm minigels (Invitrogen) with 5 µL of NativeMark™ unstained protein standards (Invitrogen). Electrophoresis was carried out at a constant voltage (150V) and at room temperature, employing 1× solutions of Anode and Cathode Running Buffers (Invitrogen) and run until the dye front reached the end of the gel (60 mm) after 90-95 minutes. Buffer compositions were obtained from the manufacture's technical guide, as shown in Table 1.

In NSDS-PAGE, 7.5 µL of protein sample were added to 2.5 µL of 4×NSDS sample buffer (100 mM Tris HCl, 150 mM Tris base, 10% v/v glycerol, 0.0185% w/v Coomassie G-250, 0.00625% w/v Phenol Red, pH 8.5, Table 1). Precast NuPAGE Novex 12% Bis-Tris 1.0 mm mini-gels (Invitrogen) were run at 200V for 30 minutes in double distilled (dd) $H_2O$ to remove storage buffer as well as any unpolymerized acrylamide. During this time, the NSDS-PAGE running buffer (50 mM Tris Base, 50 mM MOPS, 0.0375% SDS, pH 7.3, Table 1) was chilled to 4° C. Samples (including 5 µL of Pre-stained SDS-PAGE protein standards) were loaded into the gel and electrophoresis was conducted at constant voltage (150 V) at 4° C. until the dye front reached the end of the 60 mm gel after 80-85 minutes.

SDS-PAGE and NSDS-PAGE gels were stained using SimplyBlue™ Safe Stain (Invitrogen). Gels were washed 3× in dd$H_2O$ for 5 minutes, incubated in 100 mL of SimplyBlue™ Safe Stain for 1 h, destained twice in 100 mL of dd$H_2O$ for 1 hour. BN-PAGE gels were microwaved for 45 seconds in fixing solution (40% methanol and 8% acetic acid) and placed on a shaker for 30 minutes. Gels were then stained in 30% methanol, 10% acetic acid containing 0.02% Coomassie R-250, microwaved again for 45 seconds, and placed on a shaker for 30 minutes. Gels were destained twice in microwaved 8% acetic acid for 1 hour.

The commercial kit for SDS-PAGE offered by Invitrogen includes sample and running buffers shown in Table 1. Both contain SDS and EDTA. According to the recipe, the protein mixture is added to the sample buffer and heated to 70° C. with the explicit intent to denature the constituent proteins through the combined exposure to 2% LDS detergent and heat. Due to its high metal binding affinity, the presence of 0.51 mM EDTA can greatly increase the probability that metal ions will be extracted from resident metalloproteins during this preparative step. Once electrophoresis is undertaken, the sample migrates in a run buffer containing 0.1% SDS and 1 mM EDTA.

Figure 1:
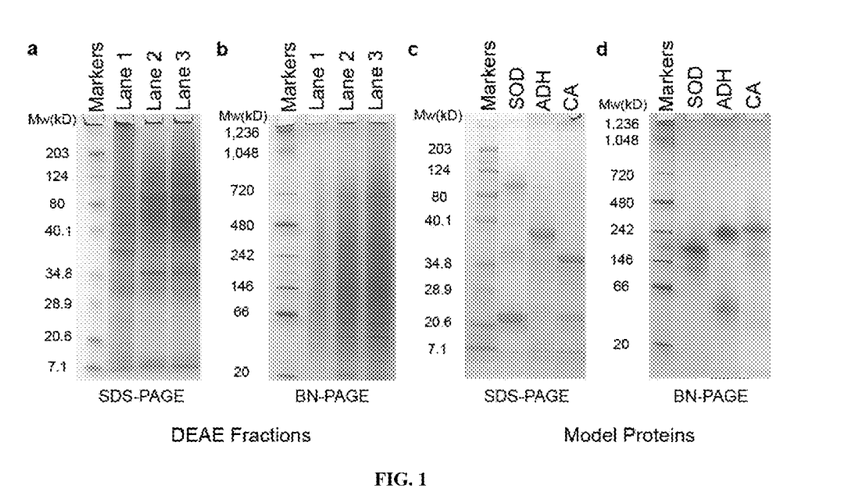
FIG. 1 shows SDS- and BN-PAGE of representative DEAE ion-exchange separated fractions of LLC-PK$_1$ supernatant and model proteins.

LLC-PK$_1$ cells were used as the source of proteome. The proteome was obtained from the gel filtration of the cellular supernatant of $5\times10^8$ LLC-PK$_1$ cells and was further separated by DEAE ion exchange chromatography. Several desalted fractions from the elution profile were subjected to SDS-PAGE using the protocol provided by Invitrogen. FIG. 1a illustrates the quality of separation of 3 DEAE fractions as visualized by Coomassie R-250 staining Many distinct protein bands were distinguishable in each of the fractions.

Figure 3:
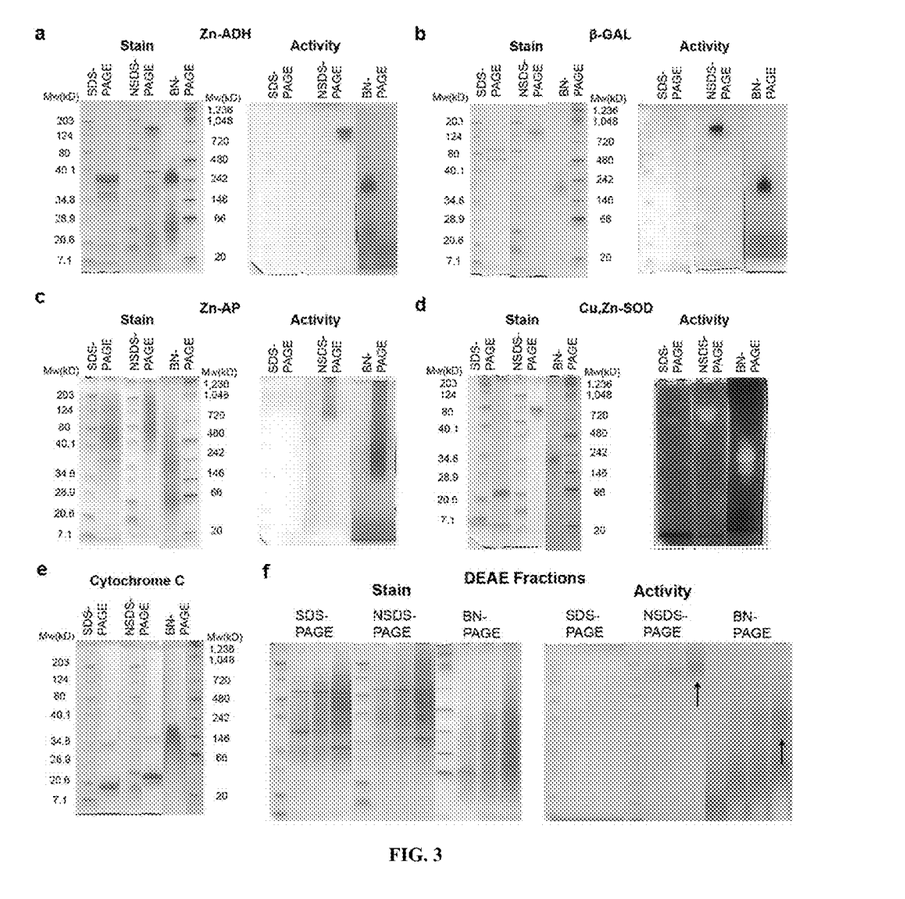
FIG. 3 shows protein migration and residual enzymatic activity after SDS-, NSDS-, and BN-PAGE.

Three Zn-proteins (Cu,Zn-SOD, Zn-ADH, and Zn-CA) were also subjected to SDS-PAGE. As seen in FIG. 1c, the extent of migration of each protein differed during electrophoresis and was related to its monomer molecular mass. Both Cu,Zn-SOD and Zn-CA electrophoresed to positions that corresponded to their approximate molecular weights. Importantly, Zn-ADH that normally exists as a 141 kDa tetramer migrated as individual 35 kDa monomers under denaturing conditions. Testing each protein for enzymatic activity showed that none of these enzymes maintained their functionality after electrophoresis (FIG. 3).

The same experiments that demonstrated the properties of SDS-PAGE were carried out to describe the behavior of proteins during BN-PAGE. Table 1 lists the buffers applied in the BN-PAGE method. LDS, SDS, and EDTA are absent and Coomassie Blue is included as a replacement for the negatively charged SDS detergent. Unlike the denaturing method, the 3 proteomic fractions were poorly separated by BN-PAGE (FIG. 1b). In the case of the model proteins, all moved to the same region of the gel, failing to separate well, in contrast to their migration pattern with SDS-PAGE (FIG. 1d). Moreover, each protein migrated to a distance inconsistent with its molecular weight. However, each displayed enzymatic activity (FIG. 3), that was maintained in the absence of the denaturating conditions present during SDS-PAGE, namely SDS, EDTA, and incubation at elevated temperature.

Figure 2:
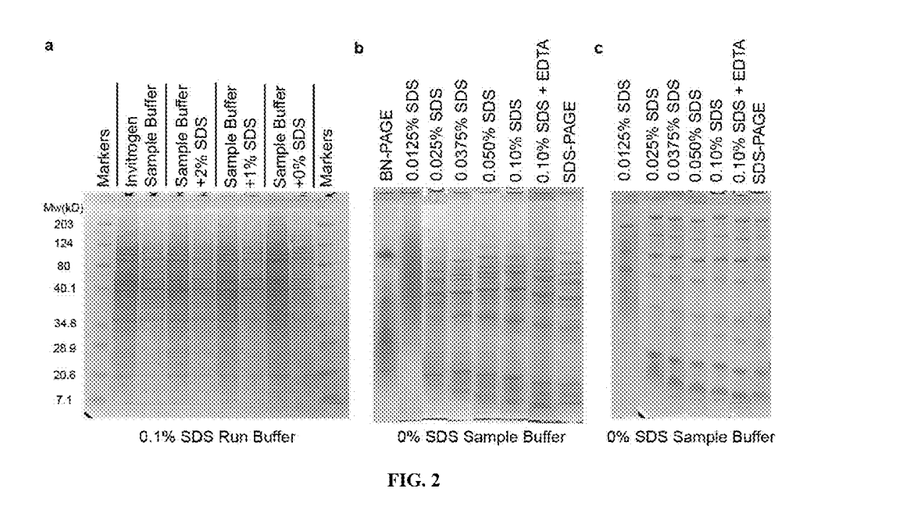
FIG. 2 shows effects of modifying SDS concentrations in the electrophoresis buffers.

Neither SDS-PAGE nor BN-PAGE was able to accomplish the goal of acceptable protein separation with retention of enzymatic activity. Thus, a new method was needed to overcome these problems. EDTA, a powerful chelator of many metal ions, was removed from both sample preparation buffer and electrophoretic running buffer to prevent direct sequestration of metal cofactors. Its deletion did not significantly impact the quality of protein separation by SDS-PAGE. In addition, the omission of the initial heating step of the protein sample in the LDS-containing loading buffer did not affect the outcome of SDS-PAGE. SDS in the sample buffer was lowered stepwise from 2% to 0% for a series of proteome samples. When the samples were electrophoresed in the standard run buffer, the results were identical to those observed with normal SDS-PAGE conditions for the sample buffer (FIG. 2a). These data indicated that detergents may not be essential in the sample buffer to obtain desirable protein resolution.

Next, the amount of SDS in the run buffer was lowered to determine the amount needed for effective resolution of protein bands. Testing BN-PAGE and the following concentrations of SDS, 0.0125%, 0.025%, 0.0375%, 0.05%, and 0.1% with a DEAE fraction of cell supernatant, resulted in poor protein separation (FIG. 2b). Furthermore, the lowest concentration of SDS was ineffective. Upon progressively increasing the SDS concentration in the run buffer, it was shown that 0.0375% SDS was a concentration that supported refined proteome separation, closely approaching that obtained with SDS-PAGE. In addition, the pre-stained SDS-PAGE protein markers were run under these conditions (FIG. 2c). Again, at 0.0375% SDS in the run buffer, the 8 proteins in the protein ladder were well separated with no significant improvement as the amount of SDS was increased in the run buffer. These buffer conditions were used to perform NSDS-PAGE and are listed in Table 1.

The electrophoretic migration of model proteins Zn-ADH, β-Gal, Zn-AP, and Cu,Zn-SOD was also examined utilizing NSDS-PAGE in tandem with SDS- and BN-PAGE (FIG. 3a-d). Unlike samples run using SDS-PAGE, proteins electrophoresed in NSDS moved a distance consistent with the molecular weights of the intact multimeric forms of the

TABLE 1

ELECTROPHORESIS BUFFERS

| | Electrophoretic Method | | |
|---|---|---|---|
| | SDS-PAGE (Invitrogen ™) | BN-PAGE (Invitrogen ™) | NSDS-PAGE |
| Sample Buffer | 106 mM Tris HCl<br>141 mM Tris Base<br>0.51 mM EDTA<br>0.22 mM SERVA Blue G-250<br>0.175 mM Phenol Red<br>2% LDS<br>10% Glycerol<br>pH 8.5 | 50 mM BisTris<br>50 mM NaCl<br>16 mM HCl<br>10% Glycerol<br>0.001% Ponceau S<br>pH 7.2 | 100 mM Tris HCl<br>150 mM Tris Base<br>0.01875% Coomassie G-250<br>0.00625% Phenol Red<br>10% Glycerol<br>pH 8.5 |
| Run Buffer | 50 mM MOPS<br>50 mM Tris Base<br>1 mM EDTA<br>0.1% SDS<br>pH 7.7 | Cathode<br>50 mM BisTris<br>50 mM Tricine<br>0.02% Coomassie G-250<br>pH 6.8<br>Anode<br>50 mM BisTris<br>50 mM Tricine<br>pH 6.8 | 50 mM MOPS<br>50 mM Tris Base<br>0.0375% SDS<br>pH 7.7 | enzymes with β-GAL migrating as dimeric species and Zn-ADH as a tetramer. In the case of Cu,Zn-SOD, the majority of the protein migrated as a multimer near 125 kDa. This high molecular weight form of SOD has been observed previously after gel filtration chromatography, corresponding to an approximate molecular weight of 130-140 kDa. In general, the protein samples migrated in tighter bands when compared to BN-PAGE and to distances more consistent with their native molecular weights. When each of the proteins subjected to NSDS-PAGE was assayed for enzymatic activity, all displayed functionality, comparable to their catalytic activity after BN-PAGE (FIG. 3a-d, right). These enzymatic functions were not observed after subjecting the enzymes to denaturing SDS-PAGE.

It is hypothesized, without being bound to any particular theory, that the reduction in concentration of SDS in the NSDS running buffer lowers the extent of binding of negatively charged SDS to proteins undergoing electrophoresis. In turn, for proteins with high pI values, it is possible that they might retain a net positive charge in the presence of SDS and not migrate in NSDS-PAGE as they do in SDS-PAGE. This question was addressed by comparing the behavior of cytochrome c from bovine heart (pI 10-10.5) in each mode of electrophoresis. FIG. 3e shows that the protein moves as a low molecular mass molecule in both SDS- and NSDS-PAGE methods. Thus, with this model protein, NSDS can facilitate the migration of a positively charged protein that is qualitatively similar to that observed with SDS.

Example 2. Characterization of Native Protein Function After Electrophoresis

In-gel (in situ) enzyme activity assays were performed based on standard protocols. In brief, model proteins or proteomic fractions from LLC-PK$_1$ extracts were run in duplicate—one for assaying activity and one for protein staining—using SDS-PAGE, NSDS-PAGE and BN-PAGE as described above. Gels were washed 3× in ddH$_2$O for 5 minutes before assays were performed.

To detect alcohol dehydrogenase (Zn-ADH) activity, gels were incubated in 50 mL of 50 mM Tris-Cl pH 8.5 buffer containing 10 mg of NAD, 10 mg of 3-(4,5-Dimethylthiazol-2-yl)-2,5-diphenyltetrazolium bromide (MTT), 0.2 mg of phenazine methosulfate (PMS) and 2 mL of 100% ethanol. Gels were incubated on a shaker in the dark until blue bands appeared, then fixed in 25% ethanol.

To measure β-galactosidase (β-GAL) activity, gels were incubated for 15 min in 50 mL of 100 mM Na$_2$HPO$_4$ buffer, pH 7.4 containing 10 mg of 5-bromo-4-chloro-indolyl-β-D-galactopyranoside (X-Gal) and 5 mg of Nitro Blue Tetrazolium (NBT). Gels were placed on a shaker in the dark until blue bands appeared (approximately 15 minutes). The reaction was halted by fixing the gel in 25% ethanol.

For the detection of superoxide dismutase (Cu,Zn-SOD), gels were submerged in 50 mL of 50 mM Tris-Cl pH 8.5 containing 10 mg of MTT, 6 mg of PMS, and 10 mg of anhydrous MgCl$_2$. The gel container was placed on a shaker exposed to light for 2 hours. Evidence of enzyme activity was the development of clear bands on a dark blue background.

For the observation of alkaline phosphatase (Zn-AP) activity, gels were soaked in 50 mL of 100 mM Tris-HCl, pH 9.0, containing 10 mg of anhydrous MgCl$_2$, 20 mg of 5-Bromo-4-Chloro-3-Indyl Phosphate, and 10 mg of NBT. After incubation on a shaker for 15 minutes in the dark, gels were fixed in 3% acetic acid. Activity was visualized by the appearance of dark blue bands.

To determine urease activity, gels were placed in 50 mL of 25 mM citrate buffer pH 6.0 containing 240 mg of urea, 10 mg of NBT, and 5 mg of dithiothreitol. The gel container was wrapped in plastic wrap and incubated on a gel shaker for 1 hour. The assay solution was replaced with 20 mM HCl and activity was visualized by the appearance of light purple bands.

To measure peroxidase activity, gels were incubated with 50 mL of 50 mM Na$_2$HPO$_4$ pH 7.0 containing 5.5 mg of NADH, 4 mg of phenol, 3 mg of NBT and 0.02% hydrogen peroxide. The gel container was sealed and incubated on a shaker for 30 minutes. The reaction ceased after the addition of 25% ethanol. A light brown band characterized the reaction product.

For the determination of carbonic anhydrase (Zn-CA) activity, gels were soaked in 50 mL of 100 mM Tris-Cl pH 9.0 containing 0.1% bromothymol blue for 15 minutes on a gel shaker. The solution was decanted and the gel was lightly blotted with a paper towel to remove excess solution. Carbon dioxide gas from dry ice in water was streamed over the gel surface and active carbonic anhydrase was visualized as faint yellow bands on a blue background.

For L-amino oxidase activity, gels were incubated in 75 mL of 65 mM NaH$_2$PO$_4$ pH 6.8 containing 10 mM L-Lysine, 5 mg NBT, and 2.5 mg PMS on a rotary shaker for 30 minutes. Gels were fixed in 25% ethanol and oxidase activity was detected by the appearance of blue bands.

For glucose-6-phosphate dehydrogenase activity, 30 mg of D-glucose, 10.6 mg of adenosine triphosphate, 10 mg of MgCl$_2$, and 20 U of hexokinase were dissolved in 50 mL of 100 mM Tris-Cl pH 8.4 and the solution was incubated at 37° C. After 2 hours, 10 mg of NAD, 10 mg of MTT, and 1 mg of PMS were added and the solution was poured over the gels. After incubating the gels on a shaker for 30 minutes, the reaction was halted using 25% ethanol. Dark blue bands signified glucose-6-phosphate dehydrogenase activity.

Gels were electrophoresed using NSDS-PAGE as described above and washed twice in 100 mL of ddH$_2$O for 5 minutes. The washed gels were transferred to a UVP EpiChemi II Darkroom UV transilluminator gel box and excited at 365 nm (long wavelength UV setting), the excitation wavelength of TSQ. Fluorescent images were recorded with a digital camera with a 470 nm emission filter using a three second exposure time. For TSQ staining, gels were soaked in 50 mL of ddH$_2$O containing 25 μM TSQ on a rotary shaker for 40 minutes and washed twice with fresh ddH$_2$O for 5 minutes before fluorescent images were recorded. Gels were then additionally incubated in 50 mL of ddH$_2$O containing 100 μM TPEN for 30 minutes before subsequent images were captured.

The UW-Milwaukee Department of Chemistry and Biochemistry maintains a Micromass Platform quadrupole ICP-MS outfitted with a hexapole collision cell. The unit is linked to a CETAC LSX-213 Laser Ablation attachment. Gels to be analyzed using LA-ICP-MS were washed in 100 mL of ddH$_2$O and vacuum-dried onto Whatman filter paper and secured in the large format ablation cell (Cetac Technologies). Lanes were ablated using a 200 μm spot size scanned at 60 μm sec$^{-1}$ with 30% laser energy set at 20 Hz and the ablated aerosol was carried to the ICP-MS at a flow rate of 1.0 L He min$^{-1}$. The inductively coupled plasma was maintained using 1350 W forward power with the argon cool gas and intermediate gas flow rates set at 13.0 L min$^{-1}$ and 1.3 L min$^{-1}$, respectively. The hexapole collision cell gas flows were set at 2.5 mL He min$^{-1}$ and 1 mL H min$^{-1}$ and metal isotopes $^{64}$Zn and $^{63}$Cu were measured using peak hopping acquisition mode. $^{13}$C was also monitored to assess signal drift over time.

The capability of NSDS-PAGE to separate native proteins as demonstrated in the last experiment led to an analysis of the cellular proteomic alkaline phosphatase activity after electrophoresis. Coomassie staining of protein in FIG. 3f showed that SDS- and NSDS-PAGE resulted in similar resolutions and patterns of distinct bands, while proteins subjected to BN-PAGE were not resolved. On a separate gel, a test for alkaline phosphatase catalytic activity was positive for both NSDS- and BN-PAGE (arrows in FIG. 3O while no activity was found after SDS-PAGE. Accordingly, in experiments involving either proteomic fractions of cell supernatant or model proteins, conditions of NSDS-PAGE retained enzymatic activity as well as provided protein band resolution.

Several other proteins besides Zn-AP, Zn-ADH, β-GAL, and Cu, Zn-SOD were subjected to the three forms of PAGE and then assayed for enzymatic activity. As shown in Table 2, with the exceptions of urease and Cu, Zn-SOD, which displayed trace activity, none of the enzymes retained functionality after SDS-PAGE. All did so after BN-PAGE and seven of nine enzymes tested were active after NSDS-PAGE. This survey suggests that many proteins are functionally active after exposure to conditions of NSDS-PAGE during and after electrophoresis.

Figure 4:
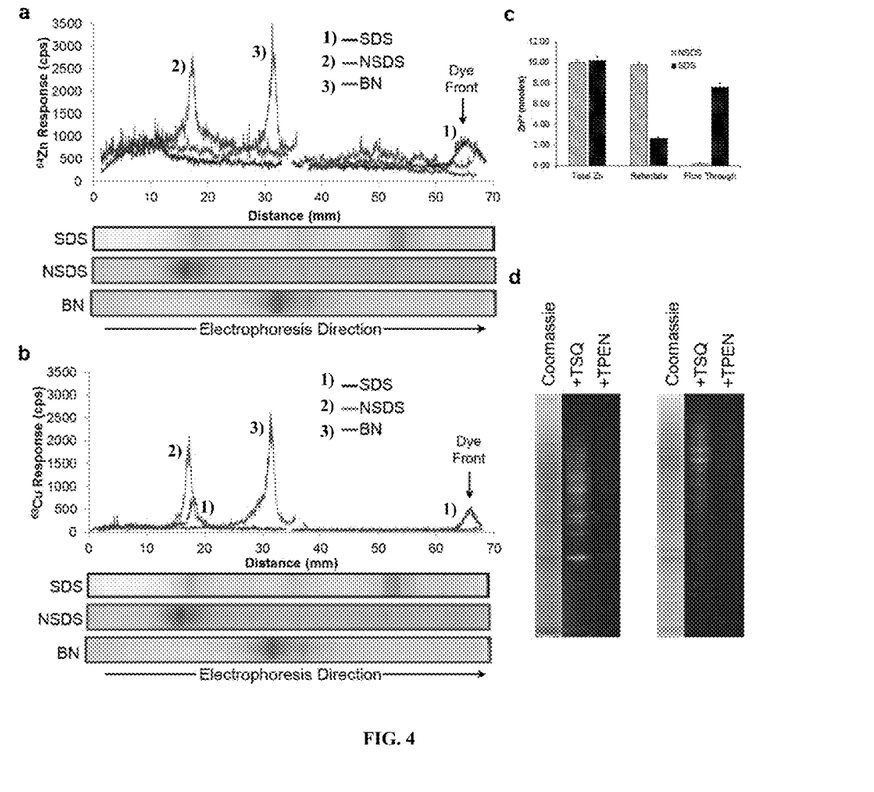
FIG. 4 shows protein metal retention after gel electrophoresis.

Cu, Zn-SOD was subjected to the three types of PAGE to assess their impact on retention of metal ions. The protein was electrophoresed and then subjected to LA-ICP-MS for metal analysis. In denaturing SDS-PAGE (blue, "1"), Zn$^{2-}$ was mobilized from SOD and recovered at the gel front (FIG. 4a, front near 65 mm). Cu$^{2+}$ was also liberated, although a minor fraction remained bound to the multimeric form of the enzyme (FIG. 4b, band near 18 mm). In contrast, both Zn$^{2+}$ and Cu$^{2+}$ were retained in comparable amounts during BN-PAGE (green, "3") and NSDS-PAGE (red, "2") (FIG. 4a-b). According to FIG. 3d, multimeric Cu-SOD that existed after SDS-PAGE showed diminished enzymatic activity, whereas Cu, Zn-SOD present after the other electrophoretic procedures displayed significant catalysis.

TABLE 2

ENZYME ACTIVITY AFTER SDS-PAGE, BN-PAGE, AND NSDS-PAGE

| Protein | Source | Activity | | |
|---|---|---|---|---|
| | | SDS-PAGE | NSDS-PAGE | BN-PAGE |
| Alkaline Phosphatase | Bovine Intestinal Mucosa | – | ++ | ++ |
| Alcohol Dehydrogenase | *Saccharomyces cerevisiae* | – | ++ | ++ |
| β-Galactosidase | *Aspergillus oryzae* | – | ++ | ++ |
| Peroxidase | Horseradish | – | ++ | ++ |
| Carbonic Anhydrase | Bovine Erythrocyte | – | ++ | ++ |
| Urease | Jack Bean | Trace | ++ | ++ |
| Superoxide Dismutase | Bovine Erythrocyte | Trace | ++ | ++ |
| L-amino oxidase | Rattlesnake Venom | – | – | ++ |
| Glucose-6-Phosphate Dehydrogenase | *Leuconostoc mesenteroides* | – | – | ++ |

To further evaluate the detrimental effects of SDS and EDTA on the metal binding capacity of the metallome, proteome from LLC-PK$_1$ cells, which includes as a sub-set the Zn-proteome, was incubated with SDS-PAGE run buffer containing 0.1% SDS and 1 mM EDTA and NSDS-PAGE buffer with 0.0375% SDS and no EDTA. After an hour's reaction, a time consistent with the duration of typical gel electrophoresis, each proteomic sample was separated from buffer by centrifugal filtration using a 3,000 Da molecular weight cut-off filter. Zn-proteome exposed to the standard SDS-PAGE running buffer lost 74±2% of its Zn$^{2+}$ to the sample buffer. In strong contrast, NSDS mobilized only 2.5±1% of its complement of Zn$^{2+}$ from the sample (FIG. 4c). Thus, exposing the proteome to standard SDS run buffer labilizes much of its bound Zn$^{2+}$, whereas negative effects on metal binding are minimized in the NSDS-PAGE run buffer.

Incubating two proteomic fractions subjected to NSDS-PAGE with TSQ form fluorescent adducts resulted in the resolution of numerous fluorescent bands in each fraction, corresponding to TSQ-Zn-protein adducts (FIG. 4d). To verify that this staining pattern was Zn$^{2+}$ dependent, the gels were subsequently soaked in a solution containing TPEN, a high affinity Zn$^{2+}$ chelator typically used in Zn-sensor experiments. Reacting TSQ-Zn-protein adducts with TPEN typically results in a decrease in fluorescence through either ligand substitution or competitive adduct formation with TSQ-Zn-proteins. Thus, the resulting depletion of TSQ-fluorescence after treatment with TPEN provides validity to the claim that Zn-proteins broadly maintained their metal cofactors after electrophoresis using NSDS-PAGE. Overall, these data support that NSDS-PAGE offers a viable method for detecting protein-bound metals after electrophoresis.

Cu,Zn-SOD was subjected to the three types of PAGE to assess their impact on retention of metal ions. The protein was electrophoresed and then subjected to LA-ICP-MS for metal analysis. In denaturing SDS-PAGE (blue, "1"), Zn$^{2-}$ was significantly mobilized from SOD and recovered at the gel front (FIG. 4a, front near 65 mm). Cu$^{2+}$ was also liberated, although a minor fraction remained bound to the multimeric form of the enzyme (FIG. 4b, band near 18 mm). In contrast, both Zn$^{2+}$ and Cu$^{2+}$ were fully retained in comparable amounts during BN-PAGE (green, "3") and NSDS-PAGE (red, "2") (FIG. 4a-b). According to FIG. 3d, multimeric Cu-SOD that existed after SDS-PAGE showed diminished enzymatic activity, whereas Cu,Zn-SOD present after the other electrophoretic procedures displayed significant catalysis.

Figure 5:
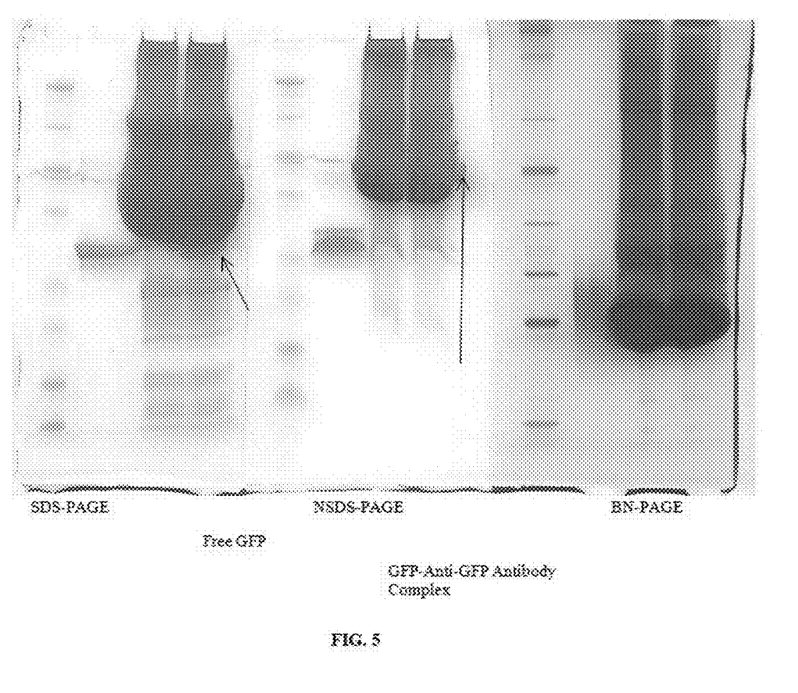
FIG. 5 shows the interaction between GFP and anti-GF in NSDS-PAGE, SDS-PAGE and BN-PAGE gels.

To test whether NSDS-PAGE maintains protein-protein interactions, 7.5 μg of GFP (lane 2), anti-GFP serum (containing GFP antibody) (lane 3), and 7.5 μg GFP+anti-GFP serum (lane 4) was electrophoresed using the SDS-, NSDS-, and BN-PAGE protocols. In the SDS-PAGE gel, GFP ran to the same position on the gel in lanes 1 and 3 (arrow), suggesting an interaction between the GFP protein and GFP antibody was not preserved. In contrast, the migration of GFP in lane 3 of the NSDS-PAGE gel was shifted to the higher molecular weight region on the gel, suggesting an intact GFP/anti-GFP protein complex. This suggests that protein-protein interactions are preserved in NSDS-PAGE while ablated in traditional methodologies.

Various features and advantages of the invention are set forth in the following claims.

What is claimed is:

1. A method of characterizing proteins, the method comprising:

(a) providing a sample comprising a plurality of proteins to be characterized, wherein the plurality of proteins are in their native form;
(b) contacting the sample from step (a) with a solution to form a sample solution;
(c) contacting the sample solution of step (b) with a gel; and
(d) separating the plurality of proteins within the sample solution by electrophoresis within the gel, wherein the gel comprises an electrophoresis solution, wherein the electrophoresis solution of step (d) comprises a detergent at a concentration of 0.03 wt % to 0.04 wt %, and the plurality of proteins maintain their native form in steps (a)-(d).

2. The method of claim 1, wherein the sample solution of step (b) is substantially free of detergent.

3. The method of claim 1, wherein the sample solution of step (b) is at a temperature of less than 30° C.

4. The method of claim 1, wherein the sample solution of step (b) is at a temperature of less than 10° C.

5. The method of claim 1, wherein the electrophoresis solution of step (d) comprises the detergent at a concentration of 0.0375 wt %.

6. The method of claim 1, wherein the detergent comprises an alkyl-sulfate compound.

7. The method of claim 6, wherein the alkyl-sulfate compound comprises sodium dodecyl sulfate.

8. The method of claim 1, wherein separating the plurality of proteins as in step (d) is performed at 4° C.

9. The method of claim 1, wherein separating the plurality of proteins within the sample solution by electrophoresis within the gel comprises separating the plurality of proteins within the sample solution by electrophoresis within the gel such that two proteins which differ in molecular weight by 2 kDa can be distinguished from one another on a 12% polyacrylamide gel.

10. The method of claim 1, wherein the native form comprises enzymatic activity.

11. The method of claim 10, wherein the enzymatic activity is provided at least in part by an enzyme that is chosen from the group consisting of dehydrogenase, galactosidase, dismutase, phosphatase, urease, oxidase, anhydrase, kinase, protease, and synthase.

12. The method of claim 1, wherein the plurality of proteins maintain their native interactions with at least one metal ion, wherein the at least one metal ion is an ion of a metal chosen from the group consisting of copper, magnesium, manganese, molybdenum, nickel, and zinc.

* * * * *

UNITED STATES PATENT AND TRADEMARK OFFICE
CERTIFICATE OF CORRECTION

PATENT NO. : 9,709,526 B2
APPLICATION NO. : 14/258160
DATED : July 18, 2017
INVENTOR(S) : David H. Petering et al.

Page 1 of 1

It is certified that error appears in the above-identified patent and that said Letters Patent is hereby corrected as shown below:

In the Specification

Column 1, Line 14:
Replace the following paragraph: "This invention was made with government support under the National Institute of Health (RO1 GM085114-01). The United States government has certain rights in the invention."

With the paragraph: ---This invention was made with government support under RO1 GM085114-01 awarded by the National Institutes of Health. The government has certain rights in the invention.---

Signed and Sealed this
Sixth Day of November, 2018

Andrei Iancu
*Director of the United States Patent and Trademark Office*